(12) United States Patent
Shinitzky

(10) Patent No.: US 6,914,056 B1
(45) Date of Patent: Jul. 5, 2005

(54) PHARMACEUTICAL COMPOSITIONS COMPRISING CYCLIC GLYCEROPHOSPHATES AND ANALOGS THEREOF FOR PROMOTING NEURAL CELL DIFFERENTIATION

(75) Inventor: Meir Shinitzky, Kfar Shmaryahu (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/936,922

(22) PCT Filed: Mar. 24, 2000

(86) PCT No.: PCT/IL00/00185
§ 371 (c)(1),
(2), (4) Date: Oct. 31, 2001

(87) PCT Pub. No.: WO00/57865
PCT Pub. Date: Oct. 5, 2000

(30) Foreign Application Priority Data

Mar. 25, 1999 (IL) ................................. 129178

(51) Int. Cl.[7] ................................. A61K 31/66
(52) U.S. Cl. .................... 514/111; 514/110; 514/105
(58) Field of Search ................ 514/110, 111, 514/105

(56) References Cited

U.S. PATENT DOCUMENTS 4,472,320 A * 9/1984 Ashani et al. ................ 558/86
5,565,439 A 10/1996 Piazza et al.
6,150,345 A * 11/2000 Chun et al. ................. 514/120

FOREIGN PATENT DOCUMENTS

WO WO 00/09139 2/2000
WO WO 00/57864 10/2000

OTHER PUBLICATIONS

Merck Index, Fifteenth edition, 1989, Merck & Co. Inc. pp. 1336–1340, 1532–1539.*
Friedman, P. et al; "Conversion of Lysophospholipids to Cyclic Lysophosphatidic Acid by Phospholipase D" *Journal of Biological Chemistry*; vol. 271, No. 2, 1996; pp. 953–957.
M. Shinitzky et al; "Induction of Intracellular Signaling by Cyclic Glycerophosphates and their Deoxy Analogues", *European Journal of Biochemistry*; vol. 267, No. 9, 2000; pp. 2547–2554.
M. Mukai et al; Inhibition of Tumor Invasion and Metastasis by a Novel Lysophosphatidic Acid; *Int. J. Cancer*; 1999; vol. 81 No. 6; pp. 918–922.

(Continued)

Primary Examiner—Shengjun Wang
(74) Attorney, Agent, or Firm—Browdy and Neimark, P.L.L.C.

(57) ABSTRACT

Cyclic glycerophosphates and analogs thereof (CGs) are shown to exert neutral promoting activities in target cells. Such activities include promotion of neuronal outgrowth, promotion of nerve growth, provision of dopaminotrophic supporting envrionment in a diseased portion of the brain, prevention of nerve degeneration and nerve rescue. These activities of the CGs render them useful for treatment of various disorders including but not limited to mental disorders such as, for example, schizophrenia, dementia or disorders resulting in learning disablities. In addition, these CGs may be used for the treatment of neurodegenerative conditions such as Altzheimer's diesease, Parkinson's disease, conditions resulting from exposure to harmful environmental factors or resulting from a mechanical injury. The CGs may also be used to treat an individual suffering from a primary neurodengenerative condition in order to prevent or reduce the appearance of secondary degeneration in additional nerves ("nerve rescue").

15 Claims, 8 Drawing Sheets

OTHER PUBLICATIONS

S. Kobayashi et al; "Tumor Metastasis Inhibitors Containing 1–0–acylglycerol–2,3–phosphates"; STN; Database Accession No. 126:220705; and JP 09 025235; 1997; Abstract Only.

S. Kobayashi et al; "Preparation of –0–acrylglycerol–2, 3–phosphates and DNA Polymerase.alpha.inhibitors containing them"; Database Accession No. 124:76506; and JP 07 258278; 1995; Abstract Only.

S. Kobayashi et al; "Method for Preparation of 1–0–acylglycerol–2,3–cyclic phosphate"; STN; Database Accession No. 123:144502; and JP 06 228169; 1994; Abstract Only.

S. Kobayashi et al; "Promoters of Protein Phosphokinase C activation Containing 1–0–acylglycerol 2,3–cyclic phosphate"; STN; Database Accession No. 123:350234; and JP 07 149772; 1995; Abstract Only.

D. C. Ayres et al; "The Organic Chemistry of Phosphorus. Part V."; *J. Chem. Soc.* 1957; pp. 1109–1114.

M. Revel et al; "Phosphorus Heterocycles. XXVIII. NMR Study of 4–monosubstituted 1,3,2–dioxa– and—dithiaphospholane Derivatives"; *Org. Magn. Reson.*; vol. 8, No. 8; pp. 399–496, 1976.

T. Ukita et al; "Organic Phosphates. I. Synthesis of 1,2–Diol Cyclic Phosphates"; *Pharm. Bull*; vol. 5; pp. 121–126; 1957.

B. Su et al; "Identification of a Putative Tumor Marker in Breast and Colon Cancer"; *Cancer Res.*; vol. 53, No. 8; pp. 1751–1754, 1993.

S. Abbott et al; "Chiral '160, 170, 180!phosphate monoesters. 1.Assymetric synthesis and stereochemical analysis of '1(R)–160, 170, 180!phospho–(S)–propane–1, 2–diol" *J. AM. Chem. Soc.*; 1978, vol. 100, No. 8, pp. 2558–2560.

R. K. Boyd et al; "Glycerol 1,2–Cyclic Phosphate in Centric Diatoms"; *Journal of Biological Chemistry*; vol. 262; No. 26, 199; pp. 12406–12408.

N. Clarke et al; Enzymatic Formation of Glycerol 1:2–Cyclic Phosphate; *Biochem J.*, vol. 153, pp. 745–747; 1976.

R. M. C. Dawson; "Advances in Phosphoglyceride Chemistry"; *Ann. Rept. Progr. Chem.* vol. 55, pp. 365–377; 1958.

R. M. C. Dawson et al; "The Enzymatic Formation of myoinositol 1:2–Cyclic Phosphate from Phosphatidylinositol"; *Biochem J.*; vol. 122, pp. 605–607, 1971.

P. Friedman et al; "Conversion of Lysophospholipids to Cyclic Lysophosphatidic Acid by Phospholipase D"; *The Journal of Biolgical Chemistry*; vol. 271, No. 2, pp. 953–957; 1996.

T. Hagg et al: Ciliary Neurotrophic factor prevents degeneration of adult rat substantia nigra dopaminergic neurons in vivo; *Proc. Natl. Acad. Sci. USA*; vol. 90, pp. 6315–6319; 1993.

E. P. Kennedy et al; "The Function of Cytidine Coenzymes in the Biosynthesis of Phospholipides"; *J. Biol. Chem.*, vol. 22, pp. 193–214; 1956.

B. Knusel et al; "Selective and Nonselective Stimulation of Central Cholinergic and Dopaminergic Development in vitro by Nerve Growth Factor, Basic Fibroblast Growth Factor, Epidermal Growth Factor, Insulin and the Insulin–like Growth Factors I and II"; *The Journal of Neuroscience*; vol. 10, No. 2, pp. 558–570, 1990.

B. Knusel et al; "Promotion of Central Cholinergic and Dopaminergic Neuron Differentiation by Brain Derived Neurotrophic factor but not Neurotrophin 3"; *Pro. Natl. Acad. Sci.* ; vol. 88; pp. 961–965, 1991.

L. F. Leloir; "The Enzymatic Transformation of Uridine Diphosphate Glucose into a Galactose Derivative"; *Biochem. Biophys. J*. vol. 33; pp. 186190; 1951.

L. H. LIn et al; "A Glial Cell Line–Derives Neurotrophic Factor for Midbrain Dopaminergic Neurons"; *Science*; vol. 260; pp. 1130–1134, 1993.

R. Markham et al; "The Structure of Ribonucleic Acid"; *J.D. Biochem J.*; vol. 52, pp. 552–557, 1952.

M. Shinitzky et al; "Formation of 1,3–Cyclic Glycerophosphate by the Action of Phospholipase C on Phosphatidylglycerol"; *The Journal of Biological Chemistry*; vol. 268; pp. 14109–14114, 1993.

N. Kinor et al; "Cyclic Glycerophosphates for the treatment of Parkinson's Disease"; *Neurosci. Lett.*; vol. 54; S24; 1999.

A. Tomac et al; Protection and Repair of the Nigrostriatal dopaminergic system by GDNF in vivo; *Nature*; vol. 373, pp. 335–339, 1995.

T. Ukita et al; "Studies on the Alkaline Hydrolysis of Lecithin: Synthesis of Cyclic 1,2–Glycerophosphate"; *J. Biol. Chem.*; vol. 216, pp. 867–874, 1955.

\* cited by examiner

PHARMACEUTICAL COMPOSITIONS COMPRISING CYCLIC GLYCEROPHOSPHATES AND ANALOGS THEREOF FOR PROMOTING NEURAL CELL DIFFERENTIATION

This application is 371 of PCT/IL00/00185, filed Mar. 24, 2000, which claims the priority of Israel Patent Application No. 129.178, filed Mar. 25, 1999.

FIELD OF THE INVENTION

The present invention concerns pharmaceutical compositions comprising cyclic glycerophosphates and analogs thereof and treatment of neural-associated conditions and disorders.

PRIOR ART

The following is a list of references which is intended for a better understanding of the background of the present invention.

Boyd, R. K., De Freitas, A. S. W., Hoyle, J., McCulloch, A. W., McInnes, A. G., Rogerson, A. and Walter, J. A., *J. Biol. Chem.*, 262:12406–12408 (1987).

Clarke, N. and Dawson, R. M. C., *Biochem. J.*, 216:867–874 (1976).

Dawson, R. M. C., *Ann. Rept. Progr. Chem.* 55:365, (1958).

Dawson, R. M. C., Freinkel, N., Jungalwala, F. B. and Clarke, N., *Biochem. J.*, 122:605–607, (1971).

Forrest, H. S. and Todd, A. R., *J. Chem. Soc.*, 1950, 3925, (1950).

Friedman, P., Haimovitz, R., Markman, O., Roberts, M. F. and Shinitzky, M., Conversion of lysophospholipds to cyclic lysophosphatidic acid by phospholipase, *D. J. Biol. Chem.*, 271:953–957 (1996).

Hagg, T. and Varon, S., *Proc. Natl. Acad. Sci.*, USA 90:6315–6319, (1993).

Kennedy and Weiss, *J. Biol. Chem.*, 222:193 (1956).

Knusel, B., et al., *Neurosci.*, 10:558–570, (1990).

Knusel, et al., *Proc. Natl., Acad. Sci.* USA, 88:961–965 (1991).

Leloir, L. F., *Biochem. Biophys., J.*, 33:186 (1951).

Linn, L. F. H., et al., *Science*, 260:1130–1134 (1993).

Markham, R. and Smith, J. D., *Biochem. J.*, 52:552- (1952).

Shinitzky, M., Friedman, P. and Haimovitz, R., Formation of 1,3-cyclic glycerophosphate by the action of phospholipase C on phosphatidylglycerol, *J. Biol. Chem.*, 268:14109–14115 (1993).

Su, B., Kappler, F., Szwergold, B. S. and Brown, T. R., *Cancer Res.*, 53:1751–1754, (1993).

Tomac, A., et al., *Nature*, 373:335–339 (1995).

Ukita, T., Bates, N. A. and Carter, H. E., *J. Biol. Chem.*, 216:867–874, (1955).

BACKGROUND OF THE INVENTION

L-α-glycerophosphate (αGP), a key constituent in phospholipid metabolism (Kennedy and Weiss, 1956), is abundant in most biological tissues (Dawson, 1958). β-Glycerophosphate (βGP) is a product of enzymatic (Ukita et al., 1955) and alkaline (Clarke and Dawson, 1976) hydrolysis of phospholipids and is formed through the cyclic phosphodiester intermediate 1,2-cyclic glycerophosphate (1,2 cGP) (Ukita et al., 1955; Clarke and Dawson, 1976). 1,2 cGP has been detected in algae species (Boyd et al., 1987) as well as in human cancer tissues (Su et al., 1993). Similarly, αGP can in principle adopt the cyclic form 1,3-cyclic glycerophosphate (1,3 cGP). This compound has been shown to be formed as an intermediate in the phospholipase C hydrolysis of phosphatidyl glycerol (PG) (Shinitzky et al., 1993) and upon further hydrolysis is converted to αGP.

A six-membered cyclic phosphate of foremost biological importance is cyclic AMP. The ring of cyclic AMP is actually a derivative of 1,3 cGP backbone. Other cyclic phosphates which were detected in biological systems include glucose cyclic phosphodiester (Leloir, 1951), 2',3'-cyclic phosphodiester (Markham and Smith, 1952), riboflavin-4',5'-cyclic phosphodiester (Forrest and Todd, 1950), myoinositol-1,2-cyclic phosphodiester (Dawson et al., 1971) and cyclic lysophosphatidic acid (Friedman et al., 1996).

Except for cyclic AMP and cyclic GMP which have been extensively studied, no specific biological activities have been so far assigned to the other biological cyclic phosphates.

There are several kinds of disorders and diseases which result from deterioration of areas of the brain and loss of neurons. One example of such diseases are neurodegenerative diseases such as Parkinson's disease (PD). Such diseases often involve degeneration of dopamine-producing neurons. Current therapeutic methods are mostly aimed at continuous stimulation of dopamine receptors by drugs which, although initially providing symptomatic relief, gradually lose effectiveness. Furthermore, such drugs do not prevent the progressive degeneration of dopaminergic neurons characteristics of such diseases.

A large number of growth factors such as nerve growth factor (NGF), basic fibroblast growth factor (bFGF), epidermal growth factor (EGF), insulin-like growth factor, brain derived growth factor and glial derived neurotrophic factor (Knusel B., et al., 1990; Knusel et al., 1991; Linn et al., 1993) stimulate dopaminergic neuron survival and differentiation in vitro. In animal models involving induction of Parkinson's disease, the induced animals show improved behavior and an increase in tyrosine hydroxylase (TH), the key enzyme in the dopamine production pathway immunoreactviity when treated with factors like GDNF (Tomac, A. et al. 1995) and ciliary neurotrophic factor (CNTF) (Hagg, T. and Varon 1993).

List of Compounds and Their Abbreviations

The following compounds which formulas are presented in Appendix A just before the claims, will be represented herein in the specification by their abbreviations as follows:

1. 1,3 cyclic glycerophosphate—1,3 cGP
2. 1,2 cyclic glycerophosphate—1,2 cGP
3. 3-acyl 1,2 cyclic glycerophosphate (cyclic lysophosphatidic acid)—c-lysoPA
4. Phenyl 1,3 cGP—P-1,3 cGP
5. Phenyl 1,2 cGP—P-1,2 cGP
6. 1,3 cyclic propanediol phosphate—1,3 cPP
7. 1,2 cyclic propanediol phosphate—1,2 cPP
8. Phenyl 1,3 cPP—P—1,3 cPP
9. Phenyl 1,2, cyclic propanediol phosphate —P-1,2, cPP
10. Cyclic dihydroxyacetone phosphate—cDHAP
11. Phenyl cyclic dihydroxyacetone phosphate —P-cDHAP Glossary The following is an explanation of some terms used above and in the following description and claims:

CG—the cyclic glycerophosphates and analogs thereof used in the present invention.

Promoting neural cell differentiation—this term relates to the capability of the CGs used in the invention to cause cells to mature into neural cells after contact therewith. Such activity may be assessed by one of many in vitro and in vivo assays such as those described in the examples below. An example for an in vitro assay would be to grow cells capable of differentiating into nerve cells (e.g. PC12 cells) in the presence of a tested compound and to determine nerve outgrowth in the cells by microscopic evaluation. In vivo assays may, for example, involve treatment of animals with injured dopaminergic neurons with the tested compounds and testing of motional and limb tremor parameters as well as in situ determination of molecules associated with dopaminergic transmission in the treated animals.

Target cells—any cells which have the potential to mature into neural cells. Non-limiting examples of such cells are PC 12 and primary brain cells.

Analog—relates to any compound which is derived from one of the cyclic glycerophosphates of the invention and which substantially maintains the activity of the cyclic phosphate from which it was derived, including, for example, deoxy analogs and phenyl esters of the cyclic glycerophosphates, preferably, deoxy analogs.

Substantially maintaining—this term relates to the capability of analogs to promote the activity carried out by the cyclic glycerophosphate from which they were derived to a certain extent. The analog's activity will be considered to be substantially maintained wherein the activity is 30% or above, preferably 50% or above, more preferably 70% or above, and most preferably 90% or above the level of the activity of the cyclic glycerophosphate.

Effective amount—wherein the method of the invention is intended for prevention of a non-desired condition, the term "effective amount" should then be understood as meaning an amount of the active compound which, when administered, results in the prevention of the appearance of the said condition. Prevention of such a condition, e.g. a neurodegenerative condition, may be required prior to the appearance of any symptoms of a disease, e.g. in individuals having a high disposition of developing the disease, or when the compositions are used for the treatment of nerve rescue which is expected after nerve injury. Wherein the compositions or methods are intended for treatment of an ongoing non-desired condition, the term "effective amount" should then be understood as meaning an amount of the active compound which is effective in ameliorating or preventing the enhancement of the treated condition and related symptoms.

Neural promoting activity—this term encompasses a variety of neural related activities which may be promoted in target cells upon their contact with the CGs used in the invention. Such activities include but are not limited to promotion of nerve growth, provision of dopaminotrophic supporting environment in a diseased brain, prevention of nerve degeneration, and nerve rescue.

Prevention or treatment—the term prevention of disorders and diseases is to be understood in accordance with the invention as a reduction in the probability of the appearance of such disorders and diseases in an individual having a high predisposition of developing such disorders and diseases, reducing the extent of the symptoms associated with such disorders and diseases when they occur or completely preventing their appearance.

Treatment of such disorders or diseases in accordance with the invention means ameliorating the symptoms associated with the disorders or diseases, reducing the extent of such symptoms or completely eliminating them.

SUMMARY OF THE INVENTION

In accordance with the invention it has surprisingly been found that 1,2 cGP, 1,3 cGP and some of their analogs are capable of promoting neuronal outgrowth of PC12 adrenal tumorigenic cells in culture after a short incubation period.

The present invention thus provides, by a first of its aspects, a pharmaceutical composition for promoting neural cell differentiation in target cells comprising a pharmaceutically acceptable carrier and, as an active ingredient, a compound of the general formula I:

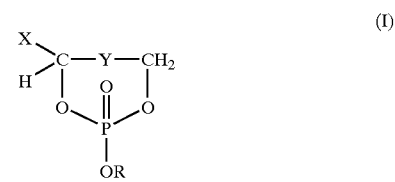

wherein
Y is —$(CH_2)_m$—, —CH(OH)— or —C(=O)—, and m is 0–3;
X is H, alkyl, —$CH_2OH$—, $CH_2$Oacyl or —$CH_2$acyl; and
R is H, a cation, alkyl or optionally substituted aryl.

As used herein the term "alkyl" refers to an alkyl group having from about 1 to about 24 carbon atoms, e.g. preferably from about 3 carbon atoms to about 20 carbon atoms, most preferably from about 5 carbon atoms to about 15 carbon atoms; the term "acyl" refers to an aliphatic saturated or unsaturated $C_1$–$C_{24}$ acyl group, preferably an acyl group having an even number of carbon atoms, most preferably an acyl group derived from a natural fatty acid such as a saturated aliphatic acyl group selected from acetyl, butyryl, caproyl, octanoyl, decanoyl, lauroyl, myristyl, palmitoyl and stearoyl, or an unsaturated aliphatic acyl group selected from palmitoleyl, oleyl, linoleyl, and ricinoleyl; and the term "aryl" refers to a mono- or poly-carbocyclic aryl group, most preferably phenyl, optionally substituted by $C_1$–$C_4$ alkyl, halogen and/or hydroxy. R may be any physiologically suitable cation and is preferably $Na^+$.

In one embodiment, Y is —CH(OH)—, X is H and R is H or phenyl. According to this embodiment, the composition comprises 1,3 cyclic glycerophosphate (1,3 cGP) or phenyl 1,3 cyclic glycerophosphate (P-1,3 cGP).

In another embodiment, Y is —C(=O)—, X is H and R is H or phenyl. According to this embodiment, the composition comprises cyclic dihydroxyacetone phosphate (cDHAP) or phenyl cyclic dihydroxyacetone phosphate (P-cDHAP).

In a further embodiment, Y is —$(CH_2)_m$—, m is 0, X is —$CH_2OH$ and R is H or phenyl. According to this embodiment, the composition comprises 1,2 cyclic glycerophosphate (1,2 cGP) or phenyl 1,2 cyclic glycerophosphate (P-1,2 cGP).

In still a further embodiment, Y is —$(CH_2)_m$—, m is 0, X is a $C_1$–$C_{24}$ alkyl, preferably —$CH_3$ and R is a cation or phenyl. According to this embodiment, the composition comprises 1,2 cyclic propanediol phosphate (1,2 cPP) or phenyl 1,2 cyclic propanediol phosphate (P-1,2 cPP).

In yet still a further embodiment, Y is —$(CH_2)$m—, m is 1, X is a $C_1$–$C_{24}$ alkyl, preferably —$CH_3$ and R is a cation or phenyl. According to this embodiment, the composition comprises 1,3 cyclic propanediol phosphate (1,3 cPP) or phenyl 1,3 cyclic propanediol phosphate (P-1,3 cPP).

In yet another embodiment, Y is —$(CH_2)_m$—, m is 0, X is —$CH_2$ ($C_1$–$C_{24}$)acyl, preferably oleyl, and R is a cation. According to this embodiment, the composition comprises 3-acyl-1,2 cyclic glycerophosphate (cyclic lisophosphatidic acid—c-lyso PA).

The CGs used in the invention may exert one of many neural promoting activities including but not limited to promotion of neuronal outgrowth, promotion of nerve growth, provision of dopaminotrophic supporting environment in a diseased portion of the brain, prevention of nerve degeneration and nerve rescue. All these activities fall within the scope of neural promoting activity.

Thus, the present invention also provides a pharmaceutical composition for promoting neural activity comprising a pharmaceutical acceptable carrier and, as an active ingredient, a compound of the general formula I above.

The ability of the pharmaceutical compositions of the invention to promote neural cell differentiation and neuronal activity in one or more of the above ways renders them extremely useful for treatment of various disorders. Thus, the invention also provides a pharmaceutical composition comprising a pharmaceutical acceptable carrier and, as an active ingredient, a compound of the general Formula I above, for the prevention or treatment of disorders and diseases which can be prevented or treated by promoting neural cell differentiation and/or neural activity.

Such disorders may be mental disorders such as, for example, schizophrenia or dementia or disorders resulting in learning disabilities.

In addition, the pharmaceutical compositions of the invention may also be used for the treatment of neurodegenerative conditions involving damage to dopaminergic neural cells. Examples of such conditions are Alzheimer's disease (AD) or Parkinson's disease (PD).

Additional neurodegenerative conditions which are within the scope of the present invention are such which result from exposure of an individual to harmful environmental factors such as hazardous chemicals, neurodegenerative conditions resulting from a mechanical injury (e.g. injury of the optical nerve resulting from contact of the eye with an abusive external factor), etc.

Furthermore, it is known that, following primary degeneration of nerves, additional nerves present in the vicinity of the degenerated nerves undergo secondary degeneration. Treatment of an individual suffering from a primary neurodegenerative condition may prevent or reduce the appearance of secondary degeneration in additional nerves present in the vicinity of the degenerated nerves. Such treatment, termed "nerve rescue" is also within the scope of the present invention.

By yet another of its aspects, the present invention provides a method for inducing promotion of neural cell differentiation of target cells comprising contacting said target cells for a suitable period of time with an effective amount of a compound of the general formula I above.

A suitable period of time is such a period which enables the compositions of the invention to exert their activity. This period of time may easily be determined by a person skilled in the art for each kind of composition and target cells using any of the methods described herewith. Typically, and in contrast to some known factors which affect neural cells such as NGF, the period of time required for the CGs used in the invention to be in contact with the target cells in order to exert their effect is very short (several minutes).

In accordance with an additional aspect of the invention, a method is provided for promoting neural activity in an individual comprising administering to the individual in need an effective amount of a compound of the general Formula I above.

A method for the prevention or treatment of disorders and diseases which can be prevented or treated by promoting neural cell differentiation and/or neural activity is also provided comprising administering to a person in need a therapeutically effective amount of a compound of Formula I above.

The method of the invention may be used for the treatment of a variety of disorders and diseases in which the abovementioned effects are beneficial, i.e., in which the effect of the CGs ameliorates or reduces the undesired symptoms of the treated condition or disease. These conditions and disorders may be for example, but not limited to, mental disorders such as schizophrenia or dementia, disorders leading to learning disabilities, neurodegenerative disorders such as Alzheimer or Parkinson disease and for prevention or treatment of nerve rescue following nerve injury.

DETAILED DESCRIPTION OF THE INVENTION

Figure 1A:
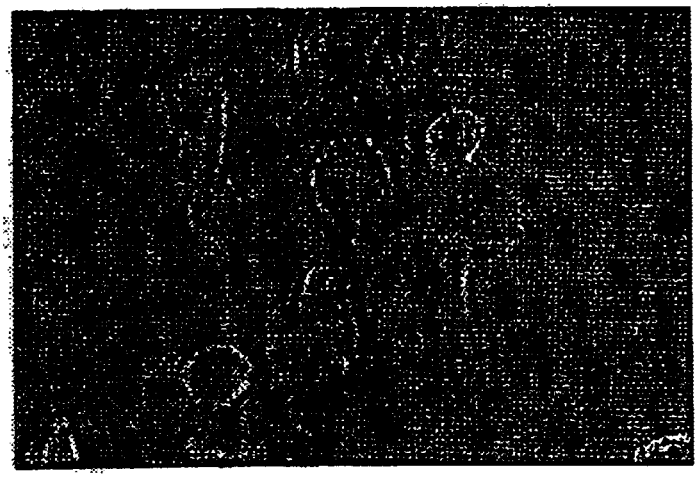
FIG. 1 shows photographs of PC12 cells following their incubation for 48 hours with growth medium containing linear a glycerophosphate as control (FIG. 1A), with nerve growth factor (NGF) at a concentration of 50 ng per/ml (FIG. 1B) and with 1,3 cyclic glycerophosphate (1,3 GP) at a concentration of 1 $\mu$M (FIG. 1C). Neuronal outgrowth is clearly seen in FIGS. 1B and 1C.

Cyclic glycerophosphates can be formed by enzymatic degradation of phospholipids which in most cases yields five or six membered ring cyclic glycerophosphates. The present invention encompasses within its scope compositions comprising both such cyclic glycerophosphates formed by enzymatic degradation of phospholipids as well as synthetically formed ones. CGs having rings of less than five or more than six carbon atoms are also included within its scope.

The cyclic glycerophosphates and analogs thereof used in the invention may generally be synthesized using any one of the methods known in the art for synthesis of phosphate esters. Specific methods which may typically be used for preparing the cyclic phosphates of the invention are described specifically below (see Examples).

Analogs of these cyclic glycerophosphates of the invention are also within the scope of the invention being typically deoxy analogs as well as phenyl esters of the 1,3 cyclic phosphates. These analogs may also be prepared by enzymatic methods or synthetically by any of the methods known in the art.

In addition to the active ingredient, the pharmaceutical compositions may also contain a carrier selected from any one of the carriers known in the art. The nature of the carrier will depend on the intended form of administration and indication for which the composition is used. The compositions may also comprise a number of additional ingredients such as diluents, lubricants, binders, preservatives, etc.

The compositions of the invention may be administered by any suitable way. A preferred mode of their administration is either i.v., topically or per os although at times it may be advantageous to use other administration modes as well.

Typically, the pharmaceutical compositions of the invention will comprise about 1 mg to about 10 mg of the active material per kg body weight of the treated individual.

While the compositions of the invention will typically contain a single CG, it is possible at times to include in the composition or to co-administer two or more CGs which may then act together in a synergistic or additive manner to prevent or treat the neurogenerative disorder.

The CGs used in the invention may be used in any of their isomer forms, (see for example, the four stereoisomers which constitute the synthetic 1,3 cGP depicted in Appendix A). For various purposes, one of the isomers may be preferred over the remaining ones.

According to the invention, the CGs may be administered either in a single dose or may be given repetitively over a period of time.

The compositions of the invention may also be administered to the treated individual in combination with an additional treatment, e.g. wherein the treated condition is a neurodegenerative one, the compositions may be given together with one of the currently available drugs or therapies used for treatment of neurodenerative diseases such as dopamine receptor stimulants, L-dopa or together with a growth factor such as NGF. In such a combination treatment the CGs may be administered simultaneously with or at different times than the administration of the additional treatment so as to yield a maximum preventive or therapeutic effect.

EXAMPLES

The invention will now be illustrated by the following non-limiting examples with reference to the appended figures.

Chemical Section

Synthesis of the Cyclic Phosphates

The cyclic phosphates of the invention are prepared by the reaction of a suitable dihydroxy compound wherein Y is —$(CH_2)_m$— or —C(=O)— and X is H or alkyl with phosphorus oxycloride ($POCl_3$) when R is H or with aryl, e.g. phenyl, phosphorodichloridate (RO—P(=O)$Cl_2$) when R is aryl.

When there is one or more hydroxy groups in the starting compound, namely Y is —CH(OH)— and/or X is —$CH_2OH$—, these hydroxy groups have to be protected, e.g. by benzylation, and the benzyl group is then removed after cyclization by conventional catalytic hydrogenation in the presence of a suitable catalyst such as Pt or Pd.

The reaction is carried out in an anhydrous solvent, e.g. dioxane or methylene chloride, in the presence of equivalent amounts of a nucleophile such as pyridine or triethylamine. The end products, when R is not aryl, are usually obtained as salts.

The synthesis of a series of known and novel 5- and 6-membered ring cyclic phosphates is illustrated below.

Example 1

Synthesis of 1,3 Cyclic Glycerophosphate (1,3 cGP)

The procedure of Buchnea (Buchnea, 1973) was followed essentially as described. Briefly, 2-benzyloxy-1,3-propanediol (Aldrich) was reacted with an equimolar amount of phosphorus oxychloride (Aldrich) in methylene chloride. The resulting 2-benzyl-1,3 cGP was treated with hydrogen under the catalysis of Pd black in methanol to remove the benzyl residue. The 1,3 cGP, isolated as the Ba salt, was pure on paper chromatography (n-propanol:ammonia:water 6:3:1, $R_f$=0.52).

1,3 cGP was also produced by the cleavage of phosphatidyl glycerol (PG) with phospholipase C as described (Shinitzky et al., 1993). The product had a trace of approx. 10–20% α-GP as indicated by paper chromatography.

Example 2

Synthesis of 1,2 Cyclic Glycerophosphate (1,2 cGP)

This compound was prepared as described (Kugel, L. and Halmann, M., *J. Am. Chem. Soc.*, 89:4125–4128 (1967). The disodium salt of β-glycerophosphate (Sigma) was first converted to the acid form and then cyclized with dicyclohexylcarbodiimide (Aldrich). The product, isolated as the Ba salt, was pure on paper chromatography.

Example 3

Synthesis of Phenyl 1,3 Cyclic Glycerophosphate (P-1,3 cGP)

The method described in Example 1 for 1,3 cGP was followed by reacting 2-benzyloxy-1,3-propanediol with phenyl phosphorodichloridate (Aldrich). The intermediate benzylated product was pure on thin layer chromatography (ethyl acetate:hexane 3:2 $R_f$=0.58), with a melting point of 136° C. It was further hydrogenated as in Example 1 to remove selectively the benzyl residue. The obtained P-1,3 cGP, compound III, was pure on thin layer chromatography (as above) with $R_f$=0.15 and melting point of 116° C.

Example 4

Synthesis of 1,3 Cyclic Propanediol Phosphate (1,3 cPP)

1,3 cPP was prepared by reacting 1,3-propanediol (Aldrich) with an equimolar amount of phosphorus oxychloride and then purified as described by Buwalda et al., 1997. The product was isolated as the free acid (melting point:99–100° C.).

$^{32}$P labeled 1,3 cPP (1,3 cP$^{32}$P) was prepared with $^{32}$POCl$_3$. The latter was obtained by introducing a trace of H$_3$$^{32}$PO$_4$ (Amersham) into an excess of POCl$_3$ in the cold (Neuhaus and Korkes, 1958). The reaction was then proceeded on a microscale and 1,3 cP$^{32}$P was isolated by co-crystallization with unlabelled 1,3 cPP.

Example 5

Synthesis of 1,2 Cyclic Propanediol Phosphate (1,2 cPP)

1,2 cPP was prepared by the same procedure as in Example 4 but using 1,2-propanediol (Aldrich). The compound was isolated as the Ba salt and was pure on paper chromatography (n-propanol:ammonia:water 6:3:1, $R_f=0.55$).

Example 6

Synthesis of Phenyl 1,3 Cyclic Propanediol Phosphate (P-1,3 cPP)

P-1,3 cPP was prepared by a method analogous to the procedure of Example 4, by reaction of 1,3-propanediol with an equimolar amount of phenyl phosphorodichloridate in dry pyridine. The product was crystallized twice from ethyl acetate-hexane and had a melting point of 72° C.

Example 7

Synthesis of Phenyl 1,2 Cyclic Glycerophosphate (P-1,2 cGP)

This novel compound was prepared as in Example 3 by reaction of 1-benzyloxy-2,3-propanediol with phenyl-$PO_2Cl_2$, followed by removal of the benzyl residue by selective hydrogenation. Crystallization was achieved from ethanol-acetone and the product had a melting point of 95° C.

Example 8

Synthesis of Phenyl 1,2 Cyclic Propanediol Phosphate (P-1,2 cPP)

This, novel compound was prepared as in Example 6 by reaction of 1,2-propanediol with an equimolar amount of phenyl-$PO_2Cl_2$ in dry pyridine. Crystallization was achieved from ethyl acetate-hexane and the product had a melting point of 69° C.

Example 9

Synthesis of Cyclic dihydroxyacetone phosphate (cDHAP)

This novel compound was prepared by reaction of $POCl_3$ with dihydroxyacetone.

1.8 g (0.01M dimer or 0.02M monomer) Dihydroxyacetone dimer MW-180 dissolved in 20 ml fresh distilled methylene chloride.

3.07 g=1.87 ml (0.02M) Phosphoryl chloride (MW-153.5, d-1.645) in 4 ml $MeCl_2$ was slowly added to the solution at RT. The solution was refluxed for 15 h (the solution was black). Methylene chloride was evaporated and 100 ml 90% acetone/water was added to the solution. The reaction mixture was refluxed for 18 h. The black solution was treated with active carbon at RT and filtered. From the resulting slightly yellow solution was evaporated acetone and water and the very nice crystalline residue was dissolved in 10 ml acetone. 0.01 M $BaJ_2$ in 80 ml acetone was added to the solution and nice crystals of cyclic-dihydroxyacetone-phosphate barium salt started to precipitate. The precipitate was washed 3 times with small quantities of acetone and dried. The product was cleaned by dissolving it in small amounts of water and precipitating with acetone. The resulting produce is white crystalline powder and shows in paper chromatography (solvents mixture:n-Propanol:$NH_4H_2O$ 6:3:1)$R_f$–0.50.

Example 10

Synthesis of Phenyl Cyclic Dihydroxyacetone Phosphate (P-cDHAP)

This novel compound was prepared by reaction of phenyl-$PO_2Cl_2$ with dihydroxyacetone in dry pyridine. Upon removal of the solvent by vacuum, the residue was extracted twice with ethyl acetate. After evaporation of the ethyl acetate, an oily residue was obtained.

Example 11

Synthesis of Cyclic Oleyl Lysophosphatidic acids (c-lysoPA)

These novel compounds were prepared by reaction of oleyl lysophosphatidic acid (Avanti Polar Lipids) with excess dicyclohexylcarbodiimide (DCC) in dimethyl sulfoxide. The product appeared as a oil.

Biological Section

Materials and Methods

The immortal PC12 cell line is one of the most investigated systems in neuronal differentiation. In the presence of nerve growth factor these cells differentiate to neuronal cells. PC12 cells originated from rat pheochromocytoma were grown as monolayers in Eagle's medium (EM) supplemented with 10% fetal calf serum, 50 µg/ml gentamicin and 5 mM glutamine, in a humidified incubator buffered with 5% $CO_2$, at 37° C. The culture medium is changed every four days and the cells are passaged every eight days and performed confluent monolayers ($1.5 \times 10^6$ in a 10 cm plate or $10^5$ cells per well in 24 wells plate). PC12 cells are originally round cells which, following several days in the presence of nerve growth factor (NGF) process nerves. Upon withdrawal of the NGF, the nerves retract and a process of apoptosis is initiated in the cells.

Induction of PD in Rats

Sprague-Dawley (SD) rats (weighing 230–250 g) are anesthetized with ketamine plus xylazine administered i.p. and their head secured in a stereotaxic frame. 6OH-DA (8 mg/4 ml) is then injected into the median-forebrain-bundle to destroy the dopaminergic terminals unilaterally (Fitoussi, N., et al. *Neuroscience*, 85(2):405–413) (1998)). Manifestations of the disease are evident within 2–3 weeks.

Dopaminergic ablation is assessed behaviorally using a rotometer test, which is based on upregulation of dopamine receptors on the lesioned side. Systemic administration of a DA agonist (apomorphine, 0.25 mg/kg s.c.) induces rotation in rats with unilateral dopaminergic ablation, with rotation occurring in the direction contralateral to the side of the lesion.

Administration of Cyclic Glycerophosphates and Analogs Thereof into the Brain

Cyclic phosphates are administered into the brain using ALZET osmotic pumps (ALZET Corporation, Palo Alto, Calif.). A canulla (30 gauge) is implanted 0.5 mm medial to the SN of rats, using a stereotaxic device after assessment of nigrostriatal lesions (rotation behavior). Cyclic phosphates are microperfused at a rate of 1 µl/h for 3 or 14 days.

Brain Dissection and Extraction

Rats are decapitated and their brains rapidly removed. The brains are then placed in a rat brain mold on ice and 0.5 mm serial sections are cut and placed on chilled microscope slides. Tissue punches are rapidly taken using a stainless steel cannula with an inner diameter of 1.1 mm, according to the following coordinates: A1.5–2.0 mm for the striatum; P5.5–5.0 mm for the SN, and include most of the desired regions. The tissue samples are immediately frozen in liquid nitrogen and stored at −70° C. until extraction. Extraction is achieved by thawing the punches and subjecting them to probe sonication (80 watts for 5 sec. with a Sonifier B-12; Branson, Danbury, Conn.) in 0.5 ml of a perchlorate solution (0.1M) containing EDTA/ethanol (0.021%) on ice. A sample (100 µl) is removed for protein analysis and the remainder is centrifuged (2000×g, 10 mins. 4° C.). The resulting supernatants (the tissue extracts) are filtered (0.45 μm Acrodisk, Gelman; Ann. Arbor. Mich.) and stored at −70° C. until subjected to ELISA analysis to determine ILS or GDNF or HPLC analysis to determine the 5-HT and 5-HIAA content.

Assessment of GDNF

The effect of cyclic glycerophosphates on the release and production of GDNF from the SVG-cells and brain tissue extracts is determined as follows. Cells are incubated for 12, 24 and 48 hours with or without cyclic phosphates. Supernatants are taken after centrifugation and analyzed for GDNF using an ELISA kit (ENDOGEN, Mass., USA and PROMEGA, Madison, USA, respectively).

Isolation of RNA

Total RNA is isolated from cultured cells or tissue extracts, using Tri Reagent™ (Boehringer Mannheim, Germany). Cells are lysed in the reagent ($10^6$ cells/1 ml reagent). Frozen tissue punches are homogenized with the reagent (50 mg tissue/1 ml) using a glass Teflon rod. Chloroform is then added and the homogenates are separated into three phases by centrifugation. Care is taken when removing the aqueous phase so as not to disturb the interphase or the organic phase, In order to avoid genomic DNA contamination, RNA is precipitated from the aqeuous phase by addition of isopropanol, washed with ethanol and solubilized in DEPC treated water. RNA is estimated spectrophotometrically at 260 nm and 280 nm and stored at −80° C. until use.

First strand cDNA synthesis is carried out in a reaction volume of 20 μl containing 3 μg of total RNA, 10 mM primer dT (Boehringer Mannheim, Germany) and 1 mM dNTP mix (Boehringer Mannheim, Germany). After heating for 2 min. at 65° C. and cooling back to 4° C., the reaction is initiated by the addition of 50 units M-MuLV reverse transcriptase and 20 units RNAse inhibitor (Boehringer Mannheim, Germany). The mixture is then brought to 37° C. for 60 mins. PCR on the cDNA was carried out in a reaction volume of 50 μl. First strand cDNA (2 μl) is added to the PCR mixture containing the following components: 0.2 mM dNTP mix (Boehringer Mannheim, Germany), 1 mM each oligonucleotide primer (primers were designed according to the published GDNF cDNA sequence. 5'-TCACCAGATAAACAAATGGC-3'{5'} and 5'-TACATCCACACCTTTTAGCG-3'{3'} corresponding to bases 81–101 and 460–480 respectively) (Biosource, Calif., USA), and 2.5 U Taq DNA polymerase (Boehringer Mannheim). Reactions are overlaid with mineral oil, and initially denatured at 94° C. for 2 min. PCR is performed using a MJ Research thermal cycler programmed for 40 cycles consisting of denaturation at 94° C. for 1 min. followed by primer annealing at 55° C. for 1 min. and primer extension at 72° C. for 1 min. At the end of the 40 cycles, the reaction mixture is kept at 72° C. for 10 min. The PCR product is electrophoretically analyzed on a 2% agarose gel containing ethidium bromide).

Immunohistochemical Assessment of the Cell Survival in the Brain

At the end of the experiment the animals are anesthetized with ketamine and xylazine i.p. and then perfused via cardiac puncture with PBS followed by 4% paraformaldehyde. The brains are then removed and post-fixed in 4% paraformaldehyde for 24 hrs and then transferred into 20% sucrose for 48 hours. Tissue sections of 35 μm are obtained using a cryostat and placed in 24 wells plate in PBS. The sections are incubated overnight in 4° C. with a primary rabbit polyclonal antibody to Tyrosine hydroxylase (TH) (Chemicon, CA, USA) or a primary mouse monoclonal antibody to glial fibrillary acidic protein (GFAP) (Chemicon, CA, USA). The sections are then washed with PBS, incubated (1 hr) with a HRP conjugated secondary antibody (sheep anti-rabbit or anti-mouse) (Chemicon, CA, USA) and washed with PBS. Then, the sections are incubated with the chromagen diaminobenzidine (DAB), counter-stained with hematoxylin, and screened by light microscopy. Positive staining for TH indicates the amount of dopaminergic-cells in the striatum and substantia nigra, i.e. dopaminergic-cells survival. Positive staining for the GFAP in the injection tract indicates glioma processes.

Microdialysis

The microdialysis technique requires implantation of a small (500 μm diameter) probe into the brain of live rats. Implanation is performed on rats as follows. A rat is anesthetized with pentobarbital, placed in a stereotaxic apparatus, a burr hole drilled through its skull accoding to stereotaxic coordinates, and a commercially available microdialysis probe (CMA/10 probe of 3 mm length, 20 kD cutoff values; Carnegie Medicine, West lafayette, Ind.) will be lowered into the striatum. Artificial cerebrospinal fluid (CSF; 145 mM NaCl, 1.2 mM $CaCl_2$, 2.7 mM KCl, 1.0 mM $MgCl_2$, pH 7.4) is perfused slowly (1 μl/min) through the probe. Small molecules will diffuse between the artificial CSF and the extracellular fluid of the brain tissue. The rats are alowed to recover for 20–24 hrs, after which dialysate is collected from the effluent of the microdialysis probe. Dialysates (30 μl during 30 mins. intervals) are collected in polyethylene tubes containing 15 μl of EDTA-ethanol (0.02/1%) as a preservative at baseline and during administration of DA antagonists via the probe. The collected dialysates are stored at −70° C. until subjected to HPLC analysis.

Analysis of Monoamines and Metabolites in Tissue Extracts and Microdialysates

The frozen tissue extracts and microdialysates are thawed, and injected directly into a HPLC apparatus (Altex Ion Pair Ultrasphere C18, 4.6 mm inside diameter 250 mm Column No. 235335) coupled to an electrochemical detector (Model 460; Waters; Milford, Mass.) with an oxidation potential of 0.70 to 0.78 V. the mobile phase consists of 2 liters of water, 0.55 g of 1-heptanesulfonic acid, 0.2 g of EDTA, 16 ml of triethylamine, 12 ml of 85% phosphoric acid, and 80 ml of acetonitrile, pumped at 0.8 ml/min. In each sample subjected to HPLC, the levels of DA, as well as its metabolites dihydroxyphenylacetic acid (DOPAC) and hornovanillic acid (HVA) are determined by this procedure.

Results

Example 12

PC12 cells were grown in culture as explained above, the cells were divided into three groups and different factors were added to the growth medium of each group for 48 hours as follows:

Group A—α glycerophosphate.

Group B—nerve growth factor (NGF) at a concentration of 50 ng/ml.

Group C—1,3 cGP at a concentration of 1 μM.

Figure 1B:
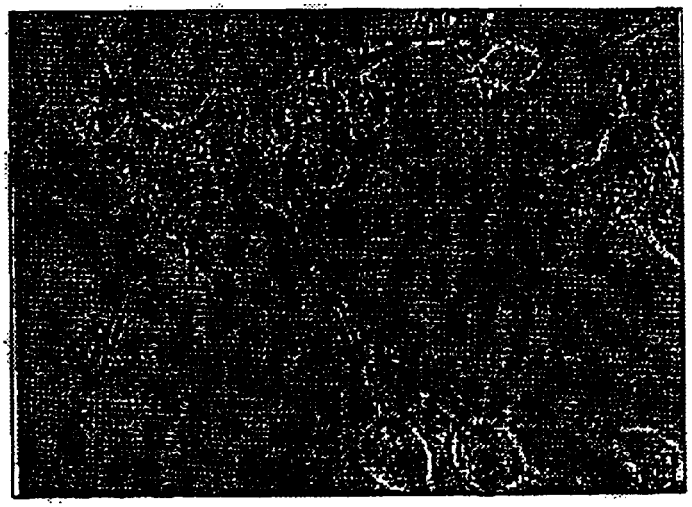
Figure 1C:
Figure 2A:
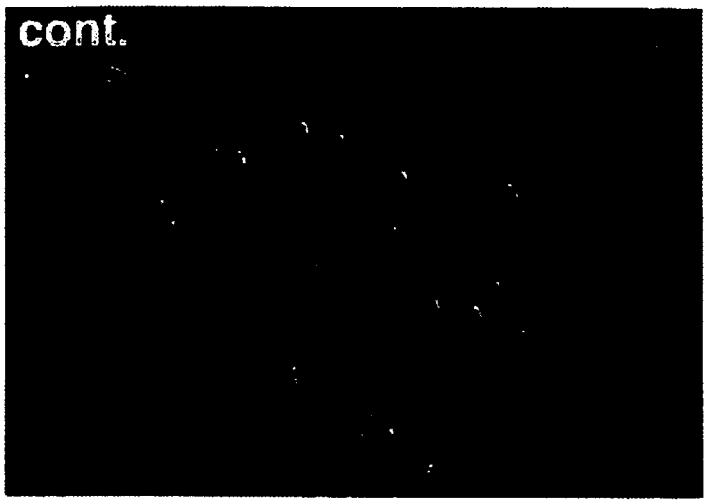
FIG. 2 shows photographs of PC12 cells grown in culture medium (control) (FIG. 2A), pulsed for three hours with linear $\alpha$ and $\beta$ glycerophosphates (FIGS. 2B and 2C, respectively) with the cyclic glycerophosphates and analogs 1,3 cGP, phenyl-1,3 cGP, 1,2 cGP, 1,3 cPP, and phenyl-1,3 cPP (FIG. 2D–FIG. 2H respectively) or with NGF (FIG. 2I). Following incubation, the cells were washed and grown in growth medium and the photographs show the cells on day 7 after treatment with the various factors. Neural outgrowth is seen only in PC12 cells treated with the above cyclic glycerophosphates and analogs (FIGS. D–H).
Figure 2B:
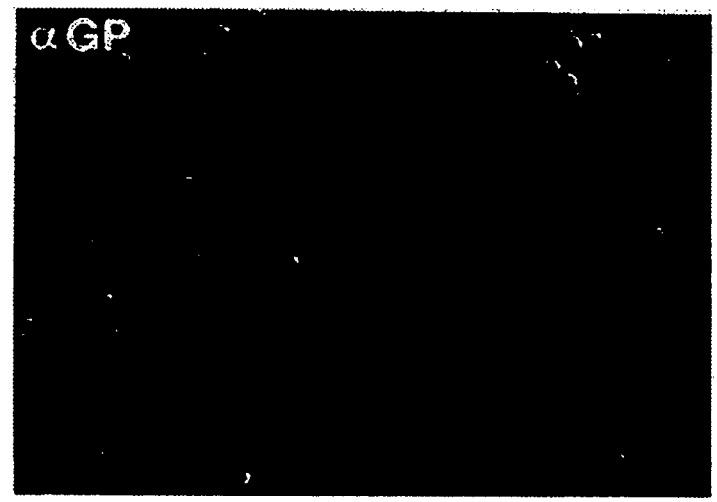
Figure 2C:
Figure 2D:
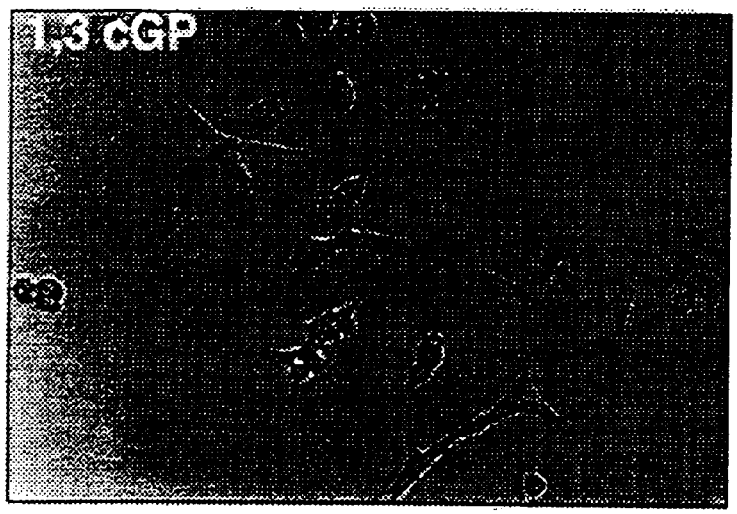
Figure 2E:
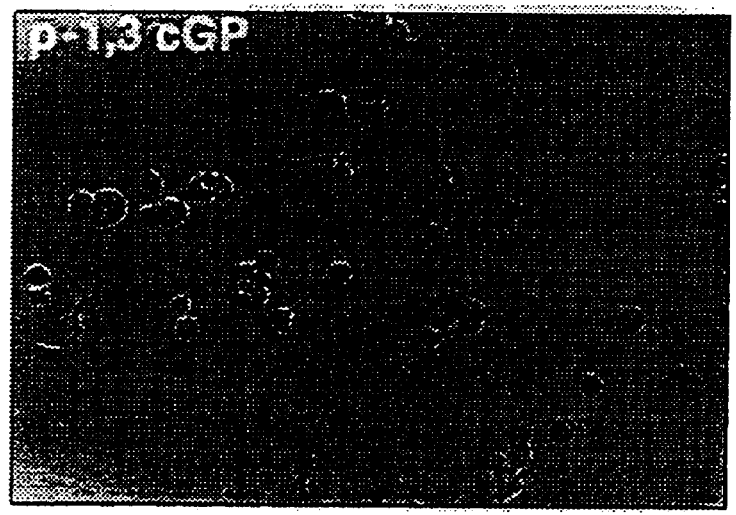
Figure 2F:
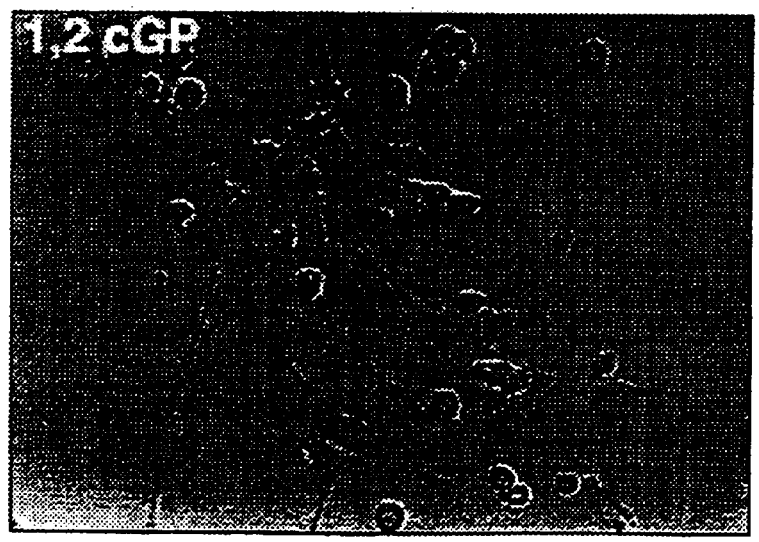
Figure 2G:
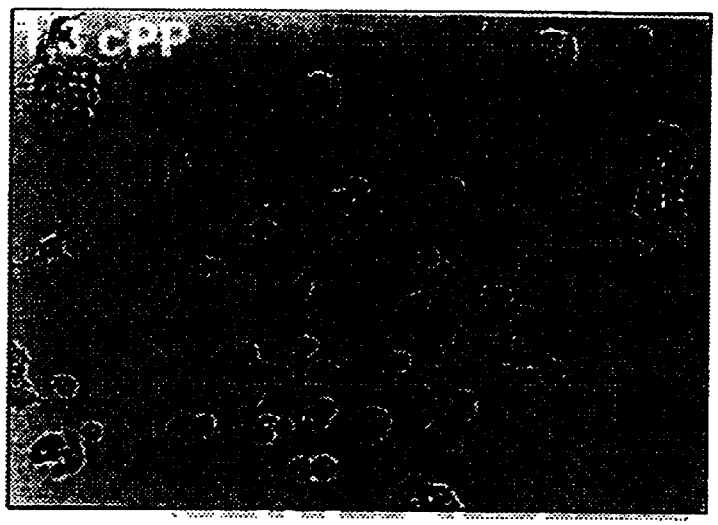
Figure 2H:
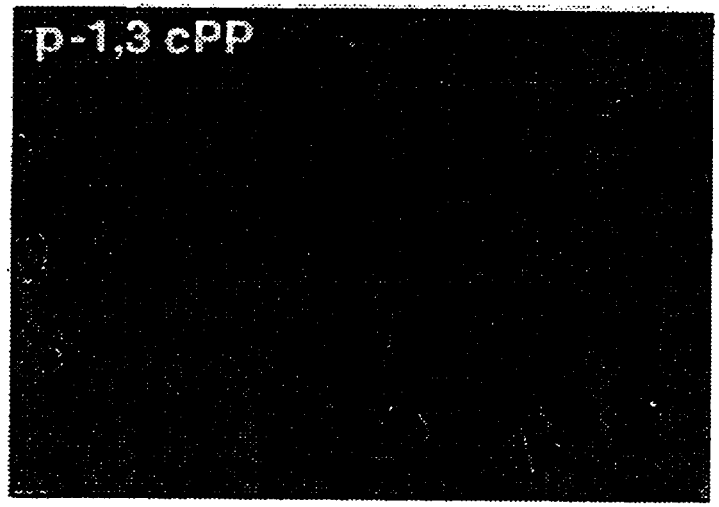
Figure 2I:
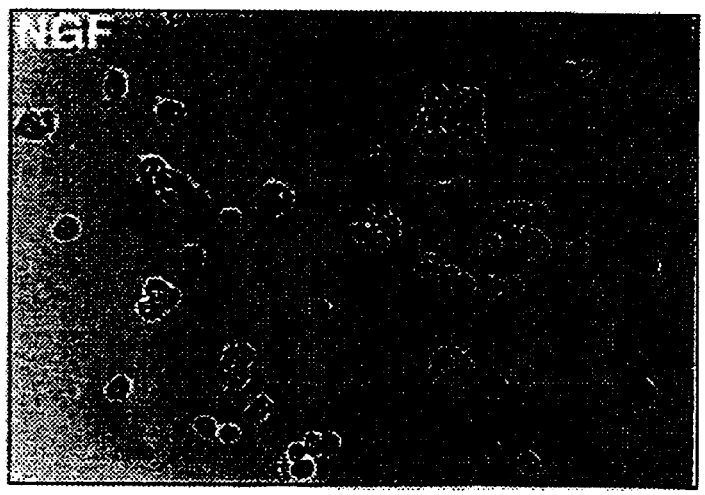

The rate of neuronal growth in each of the above cultures was monitored and documented by microscopic photographs. As seen in FIG. 1, while growth of the cells in the presence of α glycerophosphate did not promote neural outgrowth in the cells (FIG. 1A) such neural outgrowth was clearly seen in the cells which were grown in the presence of NGF (FIG. 1B) or 1,3 cGP (FIG. 1C).

Example 13

Cells were grown as described in Example 12 above with the same factors and at distinct stages the level of intercellular signaling proteins were evaluated by a Western Blot technique using antibodies specific for the tested proteins.

Example 14

Cells were grown as described above and divided into groups which were each grown with one of the following:

| (A) | growth medium | (B) | αGP           | (C) | βGP    |
|-----|---------------|-----|---------------|-----|--------|
| (D) | 1,3 cGP       | (E) | phenyl 1,3 cGP| (F) | 1,2 cGP|
| (G) | 1,3 cPP       | (H) | phenyl-1,3 cPP| (I) | NGF    |

The above factors were added to the cells for a period of three hours after which they were washed away from the cells. The cells were further grown in a growth medium which did not comprise the above factors. The neural outgrowth of the cells was monitored and microscopic photographs were taken on day seven after treatment with the above factors.

As seen in FIG. 2, under the above conditions, neural outgrowth was seen only in the cells incubated with the above CGs (FIGS. 2D–2H). No neural outgrowth was seen in the cells incubated with the linear glycerophosphates (FIGS. 2B and C) and under the above conditions NGF did not promote any nerve generation as well (FIG. 2I).

Example 15

PC12 cells were grown as described above and divided into the same groups as described in Example 14 above. The cells were incubated with the various factors for a consecutive period of seven days. Neural outgrowth was monitored and microscopic photographs were taken following the seven day incubation with the above factors.

Figure 3A:
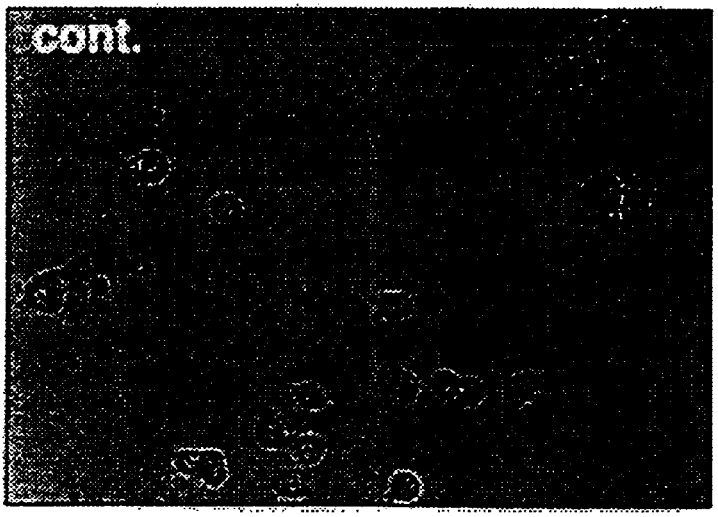
FIG. 3 shows photographs showing PC12 cells treated for a period of 7 days control medium (FIG. 3A), $\alpha$GP (FIG. 3B), $\beta$GP (FIG. 3C), the CGs: 1,3 cGP, phenyl-1,3 cGP, 1,2 cGP, 1,3 cPP, and phenyl-1,3 cPP (FIG. 2D–FIG. 2H respectively) at a concentration of 0.5 $\mu$M and with NGF (FIG. 3I). No neural outgrowth was observed after incubation with either $\alpha$ or $\beta$ GP (FIGS. 3B and C respectively) while neural outgrowth is observed to different extents in cells incubated with the various CGs (FIGS. 3D–H). Under these conditions, extensive neural outgrowth is seen in cells grown with NGF (FIG. 3I).
Figure 3B:
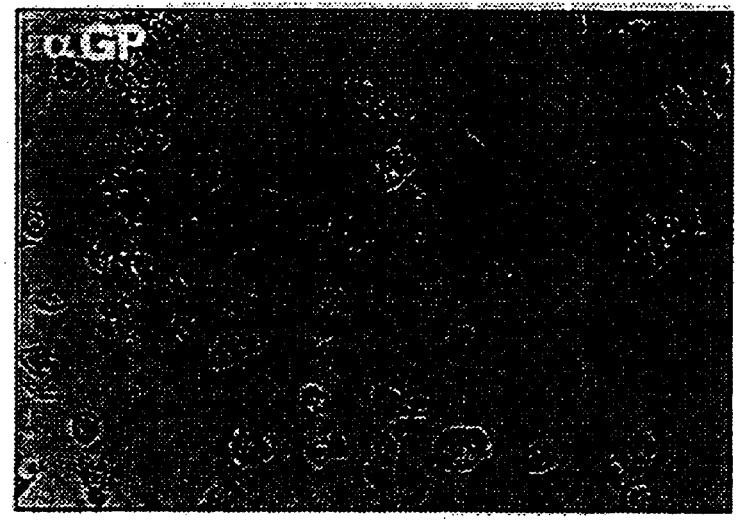
Figure 3C:
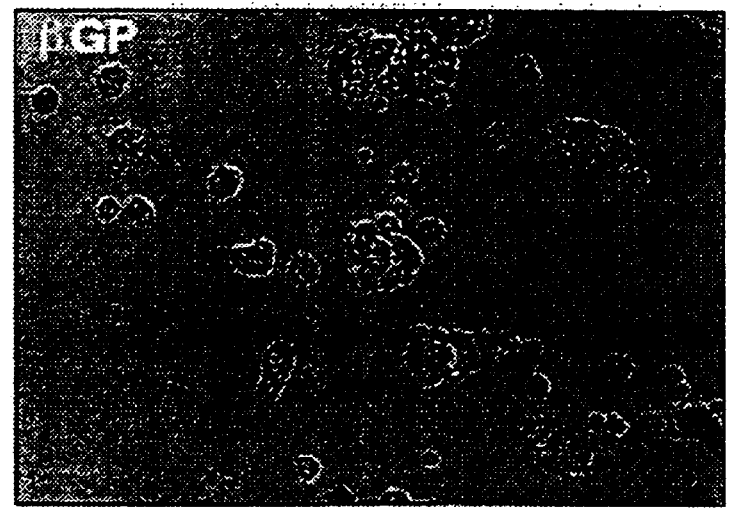
Figure 3D:
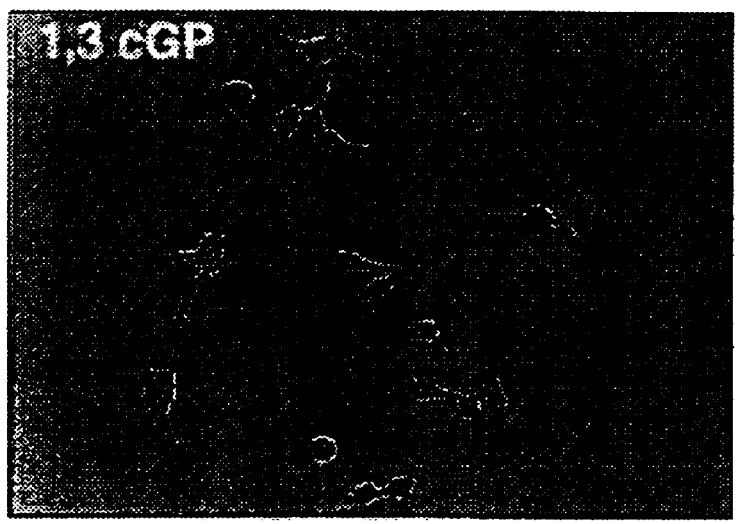
Figure 3E:
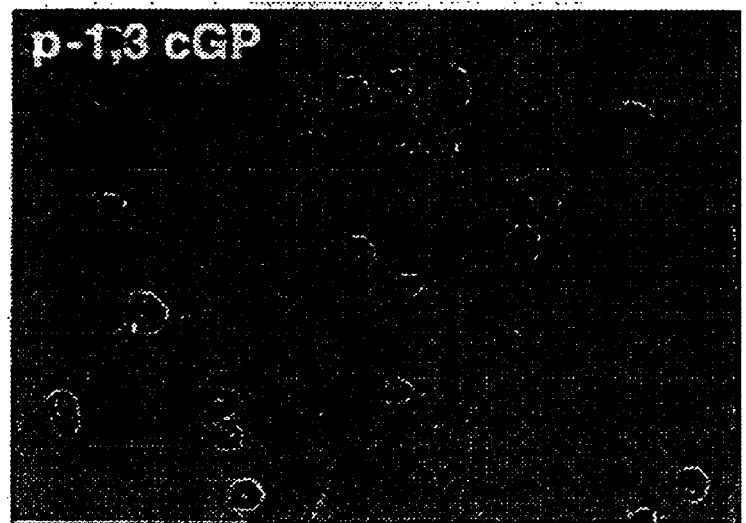
Figure 3F:
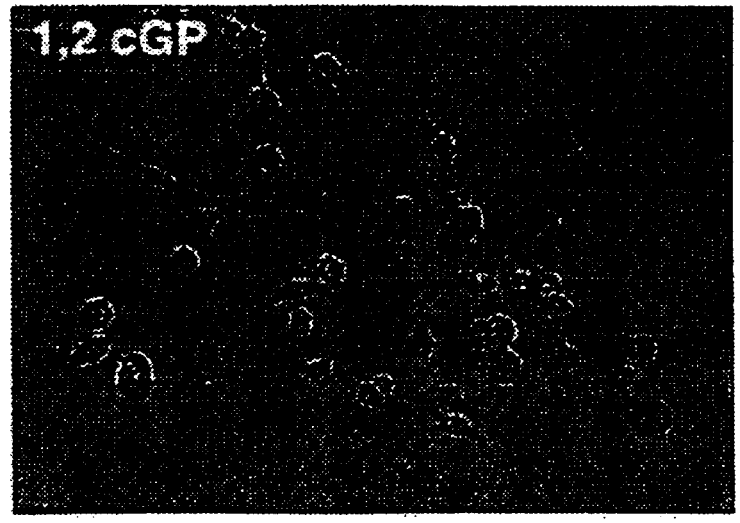
Figure 3G:
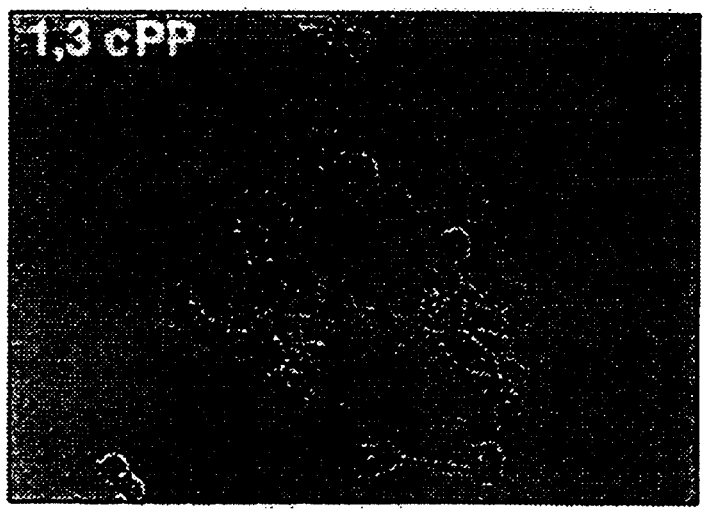
Figure 3H:
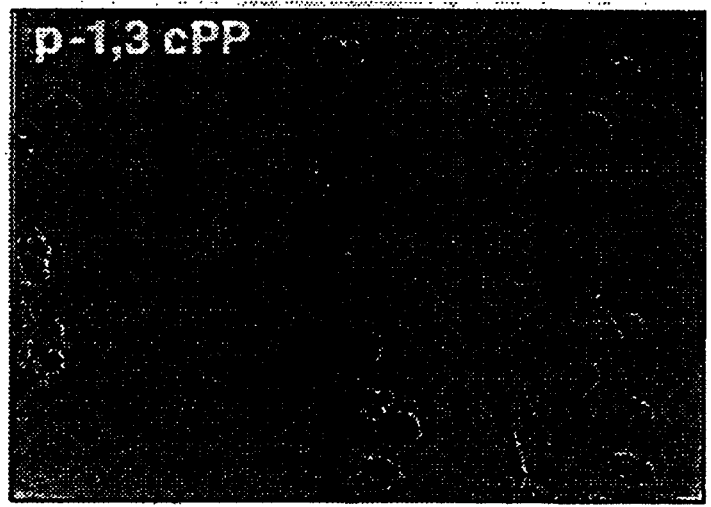
Figure 3I:
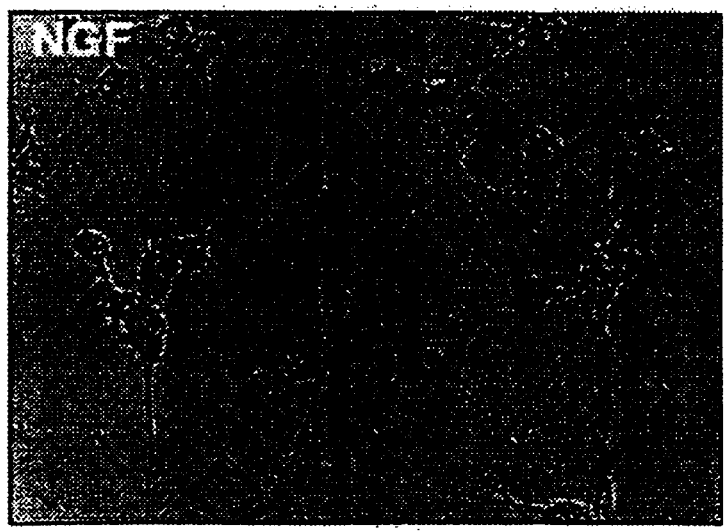

As seen in FIG. 3, neural outgrowth was seen in cells incubated with the various above CGs(FIGS. 3B–3H) as well as in cells grown in the presence of NGF (FIG. 3I) but not in the control cells grown with the linear glycerophosphates (FIG. 3A).

Example 16

PC12 cells are grown in culture in the presence of NGF under conditions allowing neuronal outgrowth of the cells. The NGF is then withdrawn by washing the cells and replacing their growth medium with a medium comprising no NGF. The cells then retract and the nerves disintegrate (analogous to the delayed neurodegeneration observed in the vicinity of injured nerves). Following this integration, the tested CG is added to the culture either for a short period of time after which it is washed or for a longer period of time and the CGs capability of "rescuing" the nerves is assessed by evaluating the re-differentiation of the cells into neuronal cells.

Example 17

Parkinson's disease is induced in rats as described in the Materials and Methods part above by injection of 6OH-DA into their brains.

The rats are then treated either with α and β linear GPs or with CG by administration of the either topically, per os, or directly into the brain using osmotic pumps as described above.

The effect of the linear GPs and of the CGs is assessed by evaluating the in situ production of L-DOPA, dopamine (DA), the dopamine metabolites DOPAC and HVA and the growth factor GDNF by using microdialysis techniques and by the methods described above. Motional and limb tremor parameters are also quantitatively evaluated in the rats treated with each of the above factors.

Example 18

Rats having injured optical nerves are treated with α and β linear glycerophosphates or with a CG as explained above and the effect of the above CG on the visual response and nerve generation of the treated rats is monitored.

Example 19

To study nerve rescue by 1,3 cPP, PC12 cells were incubated in tissue culture medium for a period of 14 days. Within this period, the cells were either grown in the presence of nerve growth factor (NGF) for different periods of times or were grown in the presence of 1,3 cPP for various periods of time. Neuronal differentiation and spread was examined in the various cells.

Figure 4A:
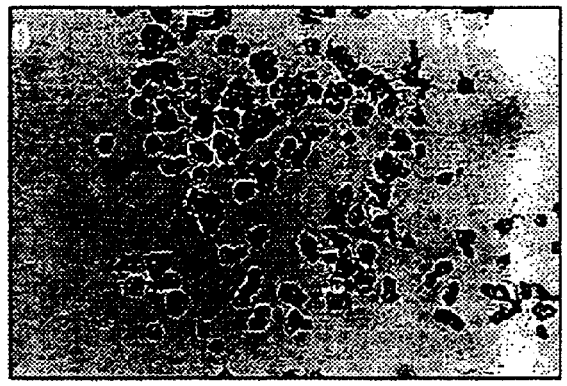
FIG. 4 shows photographs showing PC12 cells treated for 14 days with control medium (4A), with 50 ng/ml NGF (4B), treated for 7 days with 50 ng/ml NGF and then washed and treed for another 7 days either with a growth medium without NGF (4C), or with 2 $\mu$M, 4 $\mu$M or 6 $\mu$M 1,3 cPP (4D, 4E, and 4F, respectively).
Figure 4B:
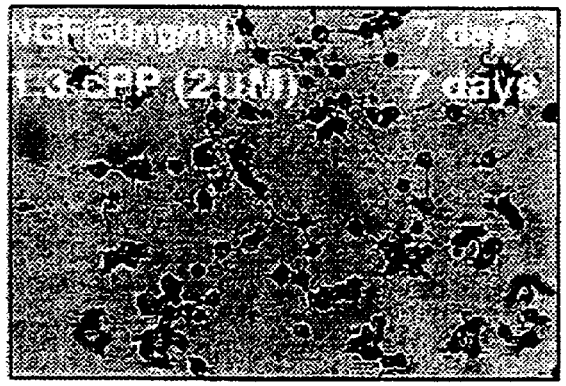
Figure 4C:
Figure 4D:
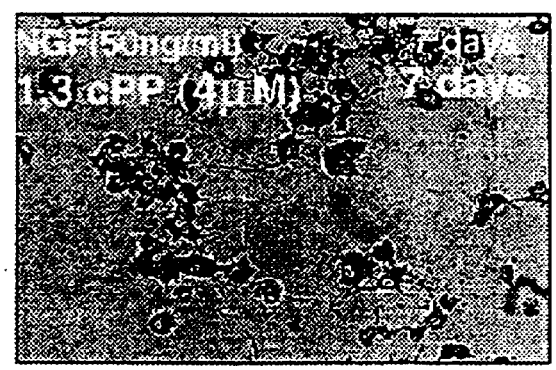
Figure 4E:
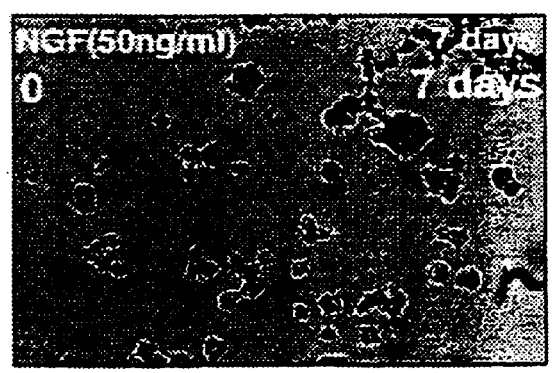
Figure 4F:
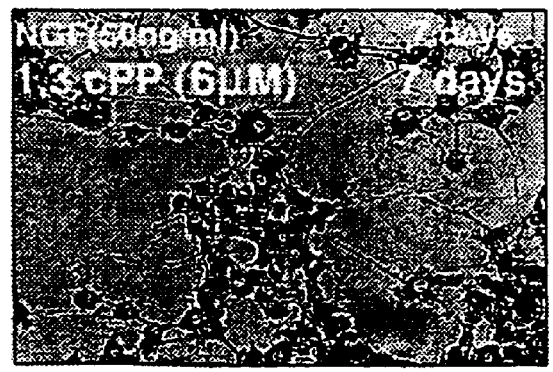

As seen in FIG. 4A, wherein the PC12 cells were grown in growth medium with no additives added, no neuronal spreading was observed (control). Growth of the cells in the presence of NGF (50 ng/ml) for the fill period of 14 days resulted in full neuronal differentiation as seen in FIG. 4B. As seen in FIG. 4C, when the cells were grown for the first 7 days in the presence of NGF (50 ng/ml) and then cultured without NGF for an additional period of 7 days, complete nerve retraction was observed and the level of differentiation of the cells returned to control level.

Wherein the PC12 cells were grown for seven days in the presence of NGF (50 ng/ml) and for the remaining 7 days with either 2 $\mu$M, 4 $\mu$M or 6 $\mu$M 1,3 cPP (FIGS. 4D, 4E and 4F, respectively) partial to full rescue of the neuronal network (which developed during the first 7 days of incubation with NGF) from retraction was observed.

APPENDIX A

| Formula | Abbreviation |
|---------|--------------|
| I  (structure shown) | 1,3 cGP |
| II (structure shown) | 1,2 cGP |
| III (structure shown) | cyclic lysophosphatidic acid, c-lypoPA |

APPENDIX A-continued

| Formula | | Abbreviation |
|---|---|---|
| IV | (structure) | P-1,3 cGP |
| V | HO—CH₂—CH—CH₂ (structure) | P-1,2 cGP |
| VI | (structure) | 1,3 cPP |
| VII | CH₃—CH—CH₂ (structure) | 1.2 Cpp |
| VIII | (structure) | P-1,3 cPP |
| IX | CH₃—CH—CH₂ (structure) | p-1,2 cPP |
| X | (structure) | cDHAP |
| XI | (structure) | P-cDHAP |

What is claimed is:

1. A method for inducing promotion of neural cell differentiation of target cells in a subject having a neurodegenerative disorder, comprising contacting said target cells for a suitable period of time with an effective amount of a compound of the general Formula I

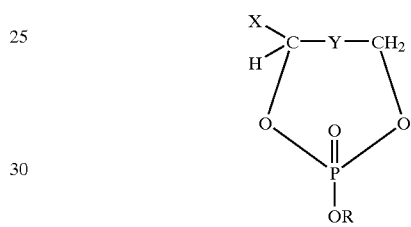

wherein

Y is —(CH₂)$_m$—, —CH(OH)— or —C(=O)— and m is 1–3;

X is H, alkyl, —CH₂OH—, CH₂Oacyl or —CH₂acyl; and

R is H, a cation, alkyl or optionally substituted aryl.

2. A method for promoting neural activity in an individual having a neurodegenerative disorder, comprising administering to the individual in need an effective amount of a compound of the general Formula I of claim 1.

3. A method according to claim 2, wherein said neural activity is selected from the group consisting of promotion of neuronal outgrowth, promotion of nerve growth, provision of dopaminotrophic supporting environment in a diseased portion of the brain and nerve rescue.

4. A method according to claim 1 wherein the compound of formula I is selected from the group consisting of i. 1,3 cyclic glycerophosphate;

ii. phenyl 1,3 cyclic glycerophosphate;

iii. 1,3 cyclic propanediol phosphate;

iv. phenyl 1,3 cyclic propanediol phosphate;

v. cyclic dihydroxyacetone phosphate; and vi. phenyl cyclic dihydroxyacetone phosphate.

5. A method for the treatment of disorders and diseases which can be treated by promoting neural cell differentiation and/or neural activity in a subject having a neurodegenerative disorder, comprising administering to a person in need a therapeutically effective amount of a compound of Formula I of claim 1.

6. A method according to claim 5, wherein said neurodegenerative disorders is dementia.

7. A method according to claim 5, wherein said neurodegenerative disorder is schizophrenia.

8. A method for promoting neural activity in an individual having a neurodegenerative disorder, comprising administering to the individual in need an effective amount of a compound of the general formula I

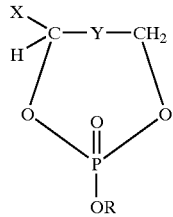

wherein

Y is —(CH$_2$)$_m$—, —CH(OH)— or —C(=O)— and m is 1–3;

X is H, alkyl, —CH$_2$OH—, CH$_2$Oacyl or —CH$_2$acyl; and

R is H, a cation, alkyl or optionally substituted aryl;

wherein said neuronal activity is selected from the group consisting of promotion of neuronal outgrowth, promotion of nerve growth, provision of dopaminotrophic supporting environment in a diseased portion of the brain and nerve rescue.

9. A method for the treatment of a neurodegenerative disorder or disease, other than dementia, which can be treated by promoting neural cell differentiation and/or neural activity, the method comprising administering to a person in need a therapeutically effective amount of a compound of Formula I

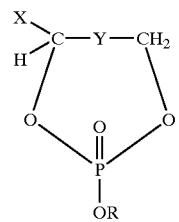

wherein

Y is —(CH2)$_m$—, —CH)OH)— or —C(=O)—, and m is 1–3;

X is H, alkyl, —CH$_2$OH—, CH$_2$Oacyl or —CH$_2$acyl; and

R is H, a cation, alkyl or optionally substituted aryl.

10. A method according to claim 9, wherein said neurodegenerative disorder is schizophrenia.

11. A method according to claim 9, wherein said neurodegenerative disorder is a learning disability.

12. A method according to claim 9, wherein said neurodegenerative disorder or disease is Alzheimer's disease or Parkinson's disease.

13. A method according to claim 9, wherein said neuro degenerative disorder or disease results from exposure of an individual to harmful environmental factors or from a mechanical injury.

14. A method according to claim 9, for the treatment of nerve rescue after a neuro-degenerative nerve injury.

15. A method according to claim 9 wherein the compound of the general formula I is selected from the group consisting of i. 1,3 cyclic glycerophosphate;
ii. phenyl 1,3 cyclic glycerophosphate-P;
iii. 1,3 cyclic propanediol phosphate;
iv. phenyl 1,3 cyclic propanediol phosphate;
v. cyclic dihydroxyacetone phosphate; and
vi. phenyl cyclic dihydroxyacetone phosphate.

* * * * *